United States Patent
Spibey (12) 
(10) Patent No.: US 9,186,398 B2
(45) Date of Patent: Nov. 17, 2015

(54) LIVE ATTENUATED PARVOVIRUS

(75) Inventor: Norman Spibey, Milton Keynes (GB)

(73) Assignee: Intervet Inc., Madison, NJ (US)

( * ) Notice: Subject to any disclaimer, the term of this patent is extended or adjusted under 35 U.S.C. 154(b) by 72 days.

(21) Appl. No.: 13/810,349

(22) PCT Filed: Jul. 18, 2011

(86) PCT No.: PCT/EP2011/062203
§ 371 (c)(1),
(2), (4) Date: Jan. 15, 2013

(87) PCT Pub. No.: WO2012/007589
PCT Pub. Date: Jan. 19, 2012

(65) Prior Publication Data
US 2013/0195913 A1    Aug. 1, 2013

Related U.S. Application Data (60) Provisional application No. 61/365,684, filed on Jul. 19, 2010.

(30) Foreign Application Priority Data

Jul. 16, 2010  (EP) .................................. 10169872

(51) Int. Cl.
| | | |
|---|---|---|
| *A61K 39/23* | (2006.01) | |
| *C07K 14/005* | (2006.01) | |
| *C12N 7/00* | (2006.01) | |
| *C12N 15/86* | (2006.01) | |
| *A61K 39/12* | (2006.01) | |
| *A61K 39/00* | (2006.01) | |

(52) U.S. Cl.
CPC ................. *A61K 39/23* (2013.01); *A61K 39/12* (2013.01); *C07K 14/005* (2013.01); *C12N 7/00* (2013.01); *C12N 15/86* (2013.01); *A61K 2039/5254* (2013.01); *A61K 2039/552* (2013.01); *C12N 2750/14322* (2013.01); *C12N 2750/14334* (2013.01); *C12N 2750/14343* (2013.01); *C12N 2750/14361* (2013.01)

(58) Field of Classification Search
None
See application file for complete search history.

(56) References Cited

U.S. PATENT DOCUMENTS

2013/0195913 A1*  8/2013  Spibey ....................... 424/201.1

FOREIGN PATENT DOCUMENTS

WO    2008157236 A1    12/2008

OTHER PUBLICATIONS

Rubio et al. (Journal of Virology. 2005; 79 (17): 11280-11290).*
Parrish et al. (Virology. 1986; 148: 121-132).*
Badgett et al., "Evolutionary Dynamics of Viral Attenuation", Journal of Virology, 2002, pp. 10524-10529, vol. 76(20).
Decaro et al., "Genetic analysis of canine parvovirus type 2c", Virology, 2009, pp. 5-10, vol. 385.
Decaro et al., "Canine parvovirus 2 strain 388/05-03 Capsid Protein (VP2) gene, compete cds.", XP-002600425, Database accession No. FJ222824, Database EMBL, (Jan. 13, 2009).
Juo et al., "SubName: Full=VP2 protein", XP-002600426, Database accession No. B5B405, Database EMBL, (Sep. 23, 2008).
Juo et al., "Canine parvovirus isolate Pfizer/vaccine/06 VP2 protein gene, completed cds", XP-002600427, Database accession No. EU914139, Database EMBL, (Aug. 18, 2008).
Mochizuki et al., "Recombination Between Vaccine and Field Strains of Canine Parvovirus is Revealed by Isolation of Virus in Canine and Feline Cell Cultures", J. Vet. Med. Sci., 2008, pp. 1305-1314, vol. 70, No. 12.
Nobivac DHPPi, Intervet/Schering-Plough Animal Health Products, XP-002600419, Sep. 9, 2010.
Yoon, Sook Hee, Molecular insights into the phylogeny of canine parvovirus 2 (CPV-2) with emphasis on Korean isolates: a Bayesian approach, Archives of Virology, 2009, pp. 1353-1360, vol. 154.
Yoon et al., "Canine parvovirus 2 strain CPVint (vaccine) VP2 (VP2) gene, complete cds", XP-002600421, Database accession No. FJ197846, Database EMBL, (Aug. 27, 2009).
Yoon et al., "SubName: Full=VP2", XP-002600422, Database accession No. B8XCVO, Database EMBL, (Mar. 3, 2009).
Yoon et al., "SubName: Full=VP2", XP-002600423, Database accession No. C7SHF6, Database EMBL, (Oct. 13, 2009).
Yoon et al., "Canine parvovirus 2 isolate CPVK7 VP2 (VP2) gene, complete cds", XP-002600424, Database accession No. FJ197829, Database EMBL, (Aug. 27, 2009).
International Search Report for corresponding PCT/EP2011/062203, mailed Sep. 12, 2011.

* cited by examiner

*Primary Examiner* — Shanon A Foley (57) ABSTRACT

The invention relates to live attenuated parvoviruses, their uses, vaccines comprising such live attenuated parvoviruses, as well as methods for their production.

17 Claims, 6 Drawing Sheets

LIVE ATTENUATED PARVOVIRUS

CROSS-REFERENCE TO RELATED APPLICATIONS

This application is a national stage entry under 35 U.S.C. §371 of PCT/EP2011/062203, filed on Jul. 18, 2011, which claims priority to U.S. Provisional Application No. 61/365,684, filed on Jul. 19, 2010, and EP Application No. 10169872.8, filed on Jul. 16, 2010. The content of PCT/EP2011/062203 is hereby incorporated by reference in its entirety.

The invention relates to live attenuated parvoviruses, their uses, vaccines comprising such live attenuated parvoviruses, as well as methods for their production.

Parvovirus belongs to the family of single stranded DNA viruses. Parvoviruses can cause disease in various animals such as cats, dogs and pigs. Because the viruses require actively dividing cells in order to replicate, the type of tissue infected varies with the age of the animal. The gastrointestinal tract and lymphatic system can be affected at any age, leading to vomiting, diarrhea and immunosuppression, but cerebellar hypoplasia is only seen in cats that were infected in the womb or at less than two weeks of age, and disease of the myocardium is seen in puppies infected between the ages of three and eight weeks.

Canine parvovirus (CPV) is a particularly deadly disease in puppies, about 80% fatal, causing gastrointestinal tract damage and dehydration as well as a cardiac syndrome in very young pups. It is spread by contact with infected dog's feces. Symptoms include lethargy, severe diarrhea, fever, vomiting, loss of appetite, and dehydration. Porcine parvovirus causes a reproductive disease in swine known as SMEDI, which stands for stillbirth, mummification, embryonic death, and infertility. Feline panleukopenia, commonly known as feline distemper, is a viral infection affecting cats, caused by feline parvovirus (FPV), a close relative of canine parvovirus. Feline panleukopenia is common in kittens and causes fever, low white blood cell count, diarrhea, and death. Infection of the cat fetus and kittens less than two weeks old causes cerebellar hypoplasia. Mink enteritis virus is similar in effect to feline panleukopenia, except that it does not cause cerebellar hypoplasia. A different parvovirus causes Aleutian Disease in minks and other mustelids, characterized by lymphadenopathy, splenomegaly, glomerulonephritis, anemia, and death. The most accurate diagnosis of parvovirus is by ELISA. Dogs, cats and swine are commonly vaccinated against parvovirus.

At the DNA level, canine, feline and porcine parvoviruses are known to have a highly homologous genome. Canine parvovirus CPV2 is a virus which is responsible for an acute and sometimes fatal enteritis in dogs (Kelly, Aust. Vet. J. 54; 593, 1978; Appel et al., Vet. Rec. 105; 156-159, 1979). The virus, which first appeared around 1977, probably arose from a very closely related virus in cats, feline panleukopaenia virus (FPLV) through a small number of mutations in the single capsid protein; a species jump which may have involved intermediate passage in other carnivores such as mink or raccoons (Truyen et al., Virology 215, 186-189, 1996).

As early as 1979 the first variants of CPV2 appeared, termed CPV2a, and they were quickly followed by the appearance of CPV2b in 1984. (Parrish et al., Science 230, 1046-1048, 1985, and J. Virol. 65; 6544-6552, 1991).

The original type 2 virus has now disappeared from the field having been replaced by the 2a and 2b types, although the relative proportions of these two types varies from country to country (Truyen et al., supra; Chinchkar et al., Arch. Virol. 151, 1881-1887, 2006; Pereira et al., Infect. Genet. Evol. 3, 399-409, 2007). The amino acid changes in the capsid protein (VP2), which characterize the shift from 2 to 2a and to 2b, are very limited. Substitutions at positions 87 (Met to Leu), 300 (Ala to Gly), 305 (Asp to Tyr) and 555 (Val to Ile) occurred in the evolution of 2 to 2a and 426 (Asn to Asp) and 555 (Ile to Val) in the emergence of 2b from 2a (Parrish et al., supra; Truyen et al., J. Virol. 69, 4702-4710, 1995). Recently, 2a strains lacking the Val to Ile substitution at position 555 have been reported (Wang et al., Virus Genes 31, 171-174, 2005; Martella et al., Virus Genes 33, 11-13, 2006). It appeared that a single amino acid change can differentiate the CPV2a and CPV2b VP2 sequences.

More recently strains have emerged in Italy in which the amino acid at position 426 (Asn in 2a and Asp in 2b) has become a glutamic acid (Glu) residue (Buonavoglia et al., J. Gen. Virol. 82, 3021-3025, 2001; Martella et al., J. Clin. Microbiol. 42, 1333-1336, 2004). The fact that these Glu 426 variants, termed CPV2c viruses, are circulating and co-existing with other CPV types in Italy and other European countries (Decaro et al., J. Vet. Med. B. Infect. Dis. Vet. Public Health 53, 468-472, 2006) and have also been isolated in countries as geographically diverse as Vietnam and Scotland (Nakamura et al., Arch Virol. 149, 2261-2269, 2004, Spibey et al., Vet. Microbiol 128, 48-55, 2008) suggests that they have an advantage in at least a proportion of the dog population.

The relatively rapid evolution of canine parvovirus has resulted in the loss and then re-gaining of the feline host range (Truyen et al., 1996 supra), and this regained ability to replicate in cats may well account for the replacement of the original type 2 virus with the 2a, 2b and 2c variants. In the late 1970s and early 1980s both live and inactivated FPL vaccines were used to protect dogs against CPV disease due to the shared antigens which stimulated cross-protection, however the level of protection they afforded was poor and duration of immunity was short. These vaccines were replaced by live attenuated CPV vaccines, which provided good protection and longer duration of immunity. Currently the live attenuated vaccines are derived from either CPV2b isolates or the original type 2 virus. Since the type 2 virus has been entirely replaced in the field by 2a, 2b and now 2c viruses there has been concern over the level of protection afforded by attenuated type 2 vaccines (Pratelli et al., Clin. Diag. Lab. Immunol. 8, 612-615, 2001; Truyen, Vet. Microbiol. 69, 47-50, 1999).

However, based on studies with available monoclonal antibodies each new antigenic variant has lost at least one neutralizing epitope compared with the former variant (Strassheim et al., Virology 198, 175-184, 1994; Pereira et al., supra). Previously it has been demonstrated that the live attenuated CPV2 vaccine is able to protect dogs against 2a and 2b field challenges (Greenwood et al., Vet. Record. 136, 63-67, 1995) even though cross-neutralization studies conducted in vitro using sera raised against the various antigenic types do show marked differences (Pratelli et al., supra).

Recently, it was shown that live attenuated type 2 vaccine (Nobivac-Intervet) was able to protect dogs from challenge with the most recent CPV variant, CPV2c (Spibey et al., Vet. Microbiol 128, 48-55, 2008).

Nevertheless there exists a need in the field for vaccines that combine the induction of a sufficient level of immunity in animals, in particular cats, dogs and pigs against infection with parvoviruses with a highly attenuated behavior. A high level of attenuation is synonymous with safety, especially in young and old animals.

It is an objective of the present invention to provide new live parvoviruses that are attenuated while still immunogenic. Such viruses provide a basis for safe vaccines.

In this respect, one embodiment of the present invention relates to live attenuated parvoviruses (PV) that comprise an amino acid other than Isoleucine at amino acid position 219 of the capsid protein and/or an amino acid other than a Glutamine at amino acid position 386 of the capsid protein (with the proviso that the PV is not the CPV that is present in canine parvovirus vaccine Nobivac Parvo C. A sequence comprised in this CPV (the CPV of canine parvovirus vaccine Nobivac Parvo C) is given in SEQ ID NO: 1.

It was surprisingly found, that these two sites, at amino acid position 219 and 386 of the capsid gene, play an important role in the attenuation of the virus. Until now it was assumed that mainly amino acids outside the capsid region are involved in the virulence/attenuation of the virus.

The location of the Isoleucine at amino acid position 219 of the capsid protein and a Glutamine at amino acid position 386 of the capsid protein is identical in both canine and feline parvoviruses, regardless of the serotype. This means that the invention can at least universally be applied to feline parvoviruses and canine parvoviruses. The invention can also be applied to e.g. Porcine parvoviruses that have an Isoleucine at amino acid position 219 of the capsid protein and/or a Glutamine at amino acid position 386 of the capsid protein.

Specifically disclaimed from the present invention is the CPV that is present in canine parvovirus vaccine Nobivac Parvo C (Intervet Schering-Plough Animal Health) that comprises the sequence as given in SEQ ID NO: 1.

Thus, a first embodiment of the present invention relates to a live attenuated parvovirus (PV), that comprises a capsid gene coding for an amino acid other than Isoleucine at amino acid position 219 of the capsid protein and/or an amino acid other than Glutamine at amino acid position 386 of the capsid protein, with the proviso that that PV does not comprise the sequence presented in SEQ ID NO: 1.

Merely to indicate the location of the Isoleucine at amino acid position 219 and the Glutamine at amino acid position 386, the two amino acids are shown below (in bold characters) in an example of the sequential context found in most CPV and FPV strains.

```
yfqwdrtlipshtgtsg    (Isoleucine 219 = bold)

yafgrqhgqkttttget    (Glutamine 386 = bold)
```

Depending upon the strain that is used as the starting material for the substitution of one or both amino acids according to the invention, it may be that a single substitution of the amino acid at position 219 or 386 is not sufficient to e.g. make the virus safe in very young animals. If a further attenuation is required, the substitution of both the amino acid at position 219 and 386 is preferred.

Therefore, a preferred form of this embodiment relates to a live attenuated parvovirus (PV) according to the invention that comprises a capsid gene coding for an amino acid other than Isoleucine at amino acid position 219 of the capsid protein and an amino acid other than Glutamine at amino acid position 386 of the capsid protein.

A more preferred form of this embodiment relates to a live attenuated parvovirus (PV), that comprises a capsid gene coding for a Valine at amino acid position 219 of the capsid protein and/or a Lysine at amino acid position 386 of the capsid protein.

An even more preferred form of this embodiment relates to a live attenuated parvovirus (PV), that comprises a capsid gene coding for a Valine at amino acid position 219 of the capsid protein and a Lysine at amino acid position 386 of the capsid protein.

If a still further attenuation is preferred, it might be attractive to use a parvovirus that already has another attenuating mutation as the starting material for the introduction of an amino acid substitution according to the invention.

Preferably, such an attenuating mutation is located outside the capsid region. This would allow for the replacement of a DNA fragment of a part of the non-capsid region of a virus according to the invention with a homologous non-capsid region of a parvovirus strain that carries an attenuation in that region. Parvoviruses carrying an attenuation in a part of the non-capsid region are e.g. the commercially available canine parvovirus vaccine Nobivac Parvo C (Intervet Schering-Plough Animal Health).

The advantage of such an approach is, that such viruses would have an even higher attenuation level. Thus, a still even more preferred form of this embodiment relates to a live attenuated parvovirus according to the invention wherein that parvovirus is a recombinant parvovirus wherein a DNA fragment of a part of the non-capsid region of said parvovirus is replaced by a homologous DNA fragment of a part of the non-capsid region derived from a second parvovirus, wherein the homologous DNA fragment of said second parvovirus carries an attenuating mutation.

A homologous DNA fragment from a second parvovirus is a DNA fragment that has the same function as the DNA fragment of the parvovirus according to the invention, but differs from that DNA fragment in that it carries a mutation that leads to attenuated behavior of the virus. Merely as an example, if a DNA fragment comprises an attenuating mutation in a DNA-fragment between two specific restriction sites, and these two restriction sites are also present at the same location in a virus not having that mutation, the restriction fragment carrying the mutation would be considered homologous with the same fragment from the virus not having that mutation.

A highly preferred form of this embodiment relates to a live attenuated parvovirus according to the invention wherein the homologous DNA fragment of said second parvovirus carries an attenuating mutation in the nonstructural region, in the region from position 2061 to 2070.

It will be understood that the live attenuated parvovirus according to the invention, regardless of the additional presence of any further attenuation, such as e.g. an attenuated non-capsid region, can be obtained from all parvoviruses in which the Isoleucine/X1 and/or the Glutamine/X2 transition according to the invention in the capsid protein can be made, and thus at least from all now sequenced members of CPV and FPV. (X1 and X2 are amino acids other than Isoleucine and Glutamine respectively).

It will also be understood, that hybrid viruses comprising an FPV-capsid and a CPV-noncapsid backbone as well as hybrid viruses comprising a CPV-capsid and an FPV-noncapsid backbone are included in the invention.

When a vaccine is to be developed for the protection of animals, more specifically pets against parvovirus infection, the preferred parvovirus for use in such a vaccine would be a canine parvovirus or a feline parvovirus.

Thus, an even more preferred form of this embodiment relates to live attenuated parvovirus according to the invention, wherein the parvovirus is a canine parvovirus or a feline parvovirus.

Especially, when a vaccine specifically aims at the protection of dogs and cats against CPV and FPV respectively, the capsid gene of the virus according to the invention would preferably encode a capsid protein of CPV serotype 2a, 2b or 2c or a capsid protein of feline parvovirus.

As mentioned above, the non-capsid part of the parvovirus can either be of CPV or FPV origin. Therefore, an even further preferred form of this embodiment relates to live attenuated CPV according to the invention, wherein the parvovirus encodes a capsid protein of CPV serotype 2a, 2b or 2c or a capsid protein of feline parvovirus.

Another embodiment of the present invention relates to vaccines for the protection of animals against infection with parvovirus, wherein such vaccines comprise a live attenuated parvovirus according to the invention and a pharmaceutically acceptable carrier.

A suitable amount of parvovirus according to the invention, for use in a vaccine would in many cases be within the range of $10^3$-$10^9$ $TCID_{50}$, depending on the level of attenuation and the replication characteristics of the virus. An infectious dose of virus that is below $10^3$ $TCID_{50}$ would in many cases be considered to be too low, since it would take too much time for the virus to replicate to a sufficiently high level to trigger the immune system. Amounts that exceed $10^9$ $TCID_{50}$ would be unattractive, if only for commercial reasons.

A very suitable dose would be in the range of $10^5$-$10^8$ $TCID_{50}$, even better between $10^6$-$10^8$ $TCID_{50}$.

Pharmaceutically acceptable carriers are well-known in the art. Merely as an example; such a carrier can be as simple as sterile water or a buffer solution such as PBS.

Vaccines according to the invention can be administered in several ways. Since the vaccine comprises a live attenuated virus, many ways of administration, such as oral, intranasal, I.M. and subcutaneous administration are feasible. A preferred route of administration is the subcutaneous administration.

Animals susceptible to parvovirus infection such as i.a. cats and dogs are frequently vaccinated against several other diseases at the same time. Therefore it would be practical to combine a vaccine according to the invention with an additional antigen of a virus or micro-organism pathogenic to dogs and cats or genetic information encoding said antigen.

Thus, another embodiment of the invention relates to a combination vaccine comprising a vaccine according to the invention and an additional antigen of a virus or micro-organism pathogenic to animals or genetic information encoding an immunogenic polypeptide of said virus or micro-organism.

The additional antigen of a virus or a micro-organism can be the whole virus or micro-organism (in a live attenuated form or in an inactivated form) or an immunogenic polypeptide or another immunogenic part of that virus or micro-organism such as e.g. a (lipo-)polysaccharide, capable of inducing a protective immune response.

Preferably, the virus or micro-organism pathogenic to animals is selected from the group of *Ehrlichia canis, Babesia gibsoni, vogeli, rossi, Leishmania donovani*-complex, Canine adenovirus, Canine coronavirus, Canine distempervirus, *Leptospira interrogans serovar canicola, icterohaemorrhagiae, pomona, grippotyphosa, bratislava*, Canine hepatitisvirus, Canine parainfluenzavirus, rabies virus, *Hepatozoon canis, Borrelia burgdorferi, Bordetella bronchiseptica*, feline Herpesvirus, feline calicivirus, feline panleucopenia and *Chlamydophila felis*.

Vaccines comprising live attenuated viruses must be stored at low temperature, or they have to be in a freeze-dried form. Freeze-dried vaccines can be kept under moderate cooling conditions or even at room temperature. Often, the vaccine is mixed with stabilizers, e.g. to protect degradation-prone proteins from being degraded, to enhance the shelf-life of the vaccine, or to improve freeze-drying efficiency. Useful stabilizers are i.a. SPGA, carbohydrates e.g. sorbitol, mannitol, trehalose, starch, sucrose, dextran or glucose, proteins such as albumin or casein or degradation products thereof, and buffers, such as alkali metal phosphates.

Therefore, preferably, the (combination) vaccine according to the invention is in a freeze-dried form. In addition, the vaccine may be suspended in a physiologically acceptable diluent. Such buffers can e.g. be sterile water, a buffer and the like.

It goes without saying, that diluents and compounds for emulsifying or stabilizing viruses are also embodied in the present invention.

Again another embodiment of the invention relates to methods for the manufacture of a (combination) vaccine according to the invention wherein these methods comprise the mixing of a live attenuated parvovirus according to the invention and a pharmaceutically acceptable carrier.

Still another embodiment of the invention relates to live attenuated parvovirus according to the invention for use as a medicament More specifically, this embodiment relates to live attenuated parvovirus according to the invention for use in the treatment of parvovirus infection.

Again another embodiment of the present invention relates to the use of a live attenuated parvovirus according to the invention for the treatment of parvovirus infection.

Finally, another embodiment of the present invention relates to methods for the preparation of a parvovirus mutant according to the invention, wherein such methods comprise exchanging a DNA fragment encoding at least part of the parvovirus capsid protein having at amino acid position 219 a codon encoding Isoleucine and/or having at amino acid position 386 a codon encoding Glutamine, by a DNA fragment encoding at least part of the parvovirus capsid protein having at amino acid position 219 a codon encoding an amino acid other than Isoleucine and/or having at amino acid position 386 a codon encoding an amino acid other than Glutamine.

Such exchanging of DNA can be done using recombinant DNA techniques well-known in the art, such as site-directed mutagenesis, exchange of restriction fragments and the like. There are several ways of making the 219 Isoleucine an X1 or 386 Glutamine an X2 substitution. Such changes could be introduced by chemical synthesis or PCR followed by recombination of the newly synthesized fragment with viral DNA.

EXAMPLES

Example 1

Production of Canine parvovirus Clone 630att Starting Materials

Viruses:

| Virus | Source | Cell substrate | Other Information |
|---|---|---|---|
| Nobivac parvo | Intervet (Nobivac parvoC vaccine vial) | A72 | Virus is a type 2 strain dating from before 1979 |
| Isolate “Jes” | Intervet inc. Millsboro USA | CrFK | Type 2c virus isolated in USA in 2008. Typing performed by DNA sequence analysis |

E. coli Strains

The E. Coli strains JC811 obtained from the E. coli genetic stock centre (USA) and strain DL795 (Kramel Biotech UK) were selected for plasmid propagation of complete infectious clones.

DNA Synthesis

Custom DNA synthesis was performed by Eurofins MWG GmbH. The synthesised DNA fragment was supplied in the pBluescrpt cloning plasmid.

The construction of the canine parvovirus clone 630att was a multi-step process and is described here in its separate steps.

1) Construction of an Infectious Molecular Clone of Nobivac Parvo C (p154att)

Figure 1:
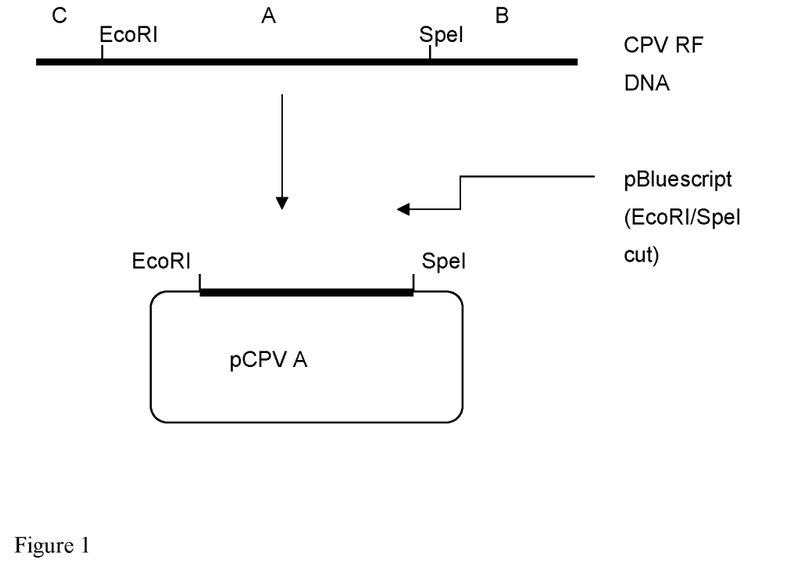
FIG. 1: Construction of pCPV A
Figure 2:
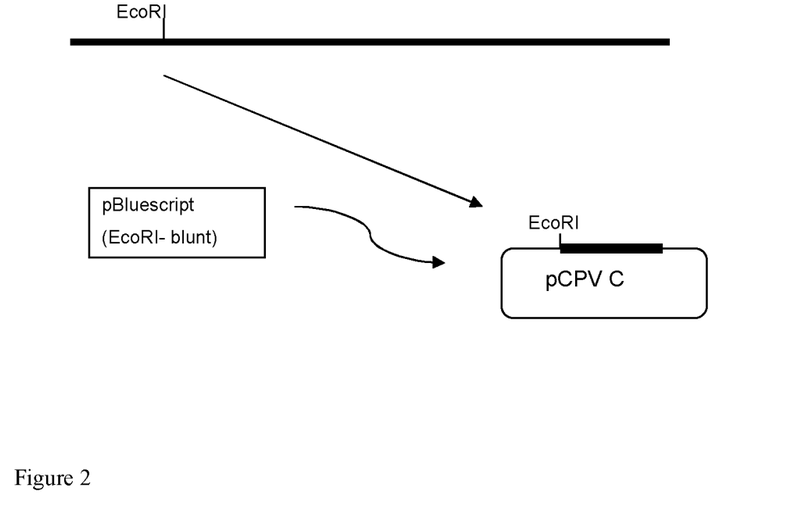
FIG. 2: Construction of pCPV C
Figure 3:
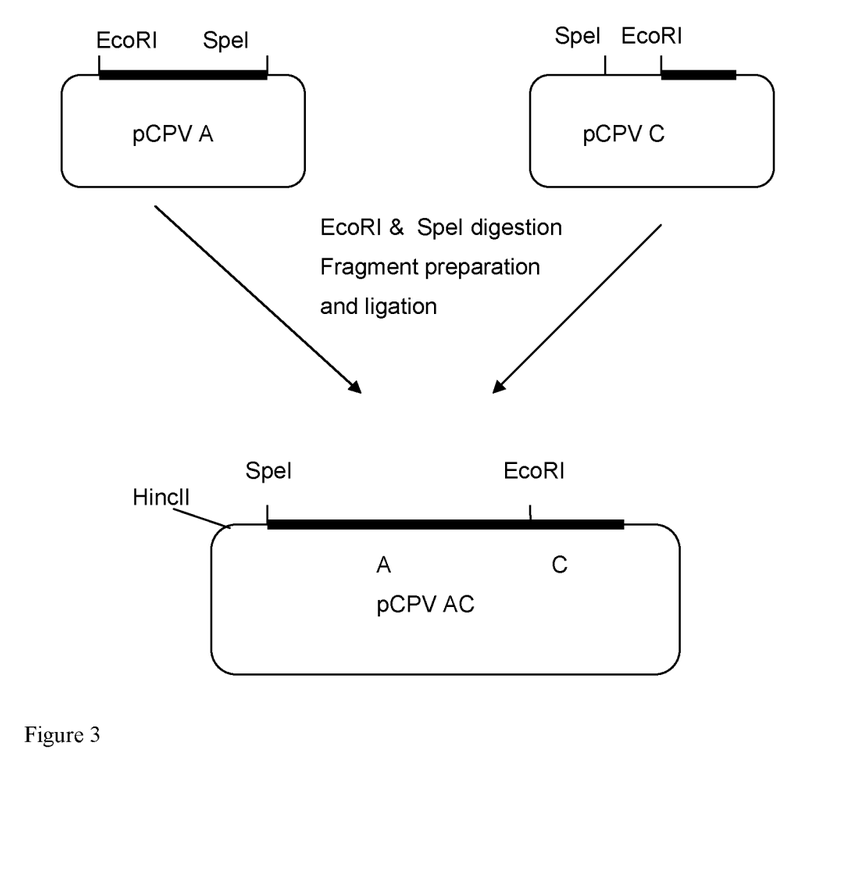
FIG. 3: Construction of pCPV AC
Figure 4:
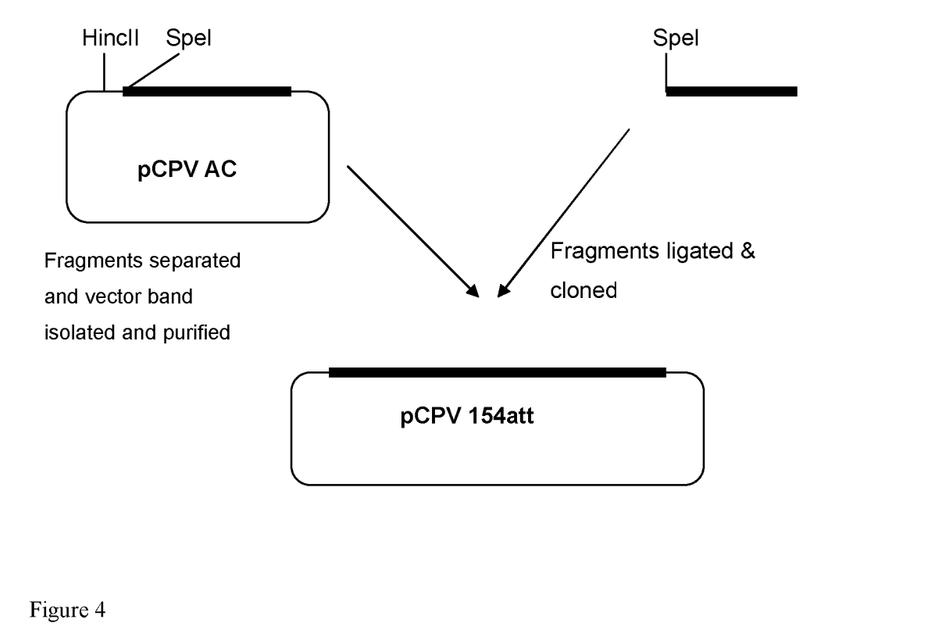
FIG. 4: Construction of pCPV 154$_{att}$

Replicative form (RF) viral DNA was obtained from A72 cells infected with Nobivac Parvo C infected cells using a modified "Hirt" preparation method (Parrish et al 1988, Virology 166, 293-307). Viral DNA was digested with a number of restriction enzymes and the genome was assembled in pBluescript using routine cloning methodology. The cloning scheme is outlined in FIG. 1-4. RF DNA of CPV 154att was first "end filled" using T4 DNA polymerase. The DNA was then digested with EcoRI and SpeI. These enzymes cut once at positions 1099 and 3459 respectively. This digestion results in three fragments labelled A, B & C in order of their size. Fragments were separated by gel electrophoresis and the EcoRI/SpeI fragment (fragment A) was then cloned into plasmid pBluescript which had been prepared by digestion with the same enzymes (see FIG. 1). The EcoRI terminal fragment (fragment C) from the RF DNA digest was then cloned into pBluescript digested with EcoRI and EcoRV to produce pCPV C (see FIG. 2).

The canine parvovirus A and C fragments were sub-cloned together into the into the same plasmid. Plasmids pCPV A and PCPV C were digested with SpeI and EcoRI. The CPV insert was purified from pCPV A and the vector portion was taken from pCPV C. Ligation then resulted in a plasmid in which fragments A and C were "re-united" (see FIG. 3).

The SpeI terminal fragment (fragment B) from the CPV RF DNA digest was then cloned into pCPV AC. Plasmid pCPV AC was digested with Spe I and an enzyme HincII which cuts leaving a blunt ends. The fragments were ligated and cloned. (see FIG. 4).

The resultant plasmid was called p154att.

Confirmation that a complete clone had been assembled was achieved by transfection of the plasmid DNA in to A72 cells resulting in the production of infectious virus.

DNA sequence analysis of the plasmid clone was performed; this sequence was shown to be identical to that determined from viral DNA extracted from infected cells, as shown further below.

2). Construction of 2/2c Hybrid D9

Figure 7:
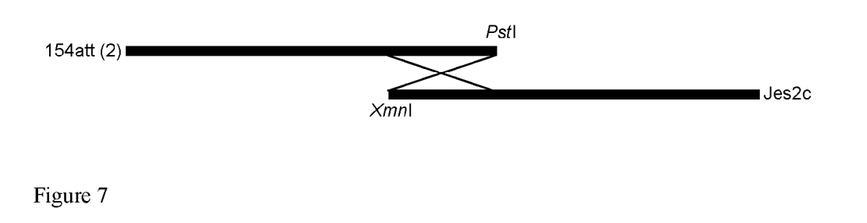
FIG. 7: schematic representation of the natural recombination (non-GM) method of obtaining a hybrid 2/2c virus isolate. Two overlapping fragments from the type 2 vaccine and type 2c field virus were transfected into cells and virus isolated following homologous recombination.

Viral DNA was obtained from both Nobivac parvo C infected cells and separately from CPV2c "Jes" infected cells. Viral DNA preparations were each digested with a single restriction enzyme to produce 2 DNA fragments from each. The enzyme digests were done in such a way that the left hand fragment of the Nobivac genome and the right hand fragment of the "Jes" genome shared >200 bp of overlapping sequence. The Nobivac left end and "Jes" right end fragments were separated purified and mixed (FIG. 7).

Transfection of A72 and CrFK cells with these overlapping fragments allowed infectious virus to be produced by natural recombination. The resulting virus was cloned by limiting dilution and termed 2/2c hybrid D9.

3). Construction of Clone 630.

Clone 630 was developed from the infectious plasmid clone p154att and DNA prepared from 2/2c hybrid D9.

Figure 5:
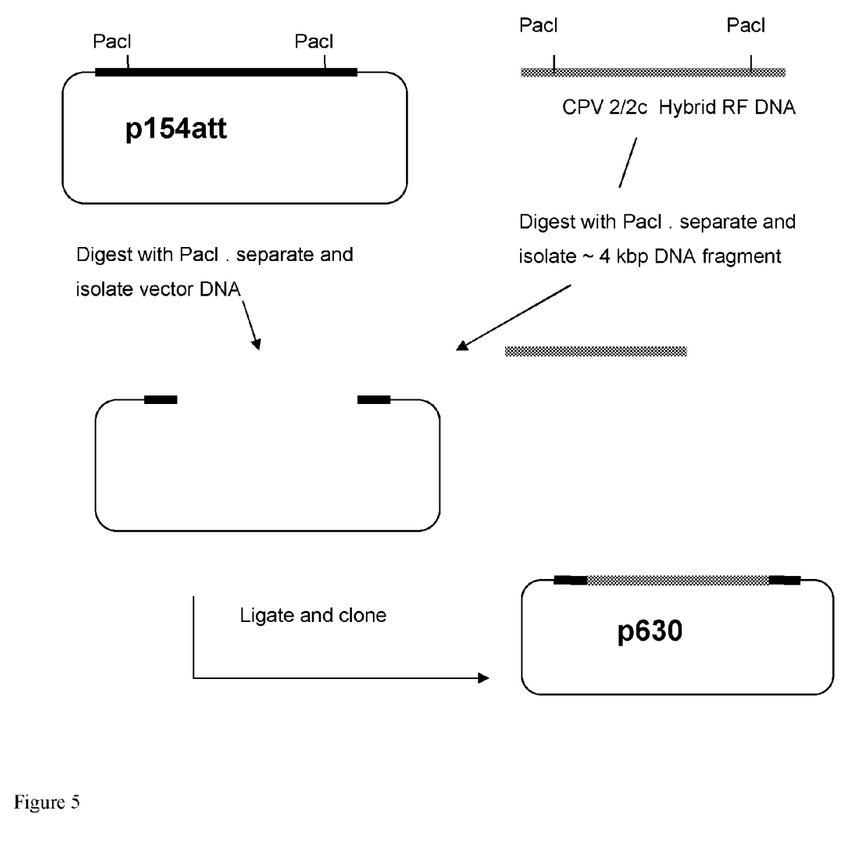
FIG. 5: Construction of p630

The restriction enzyme PacI cuts the CPV genome in two places around positions 561 and 4651; the far left and right ends of the genome. Therefore the plasmid p154att was digested with PacI and the ~4 kbp PacI fragment containing over 80% of the genome was separated from the vector and terminal sequences and replaced with that obtained from 2/2c hybrid D9 DNA. The resultant plasmid was termed p630. This is illustrated in FIG. 5.

As predicted, transfection of A72 or CrFK cells with p630 results in the generation of infectious virus, this virus is termed 630.

Virus 630 like 2/2c hybrid D9 retained a low level of pathogenicity.

4). Construction of Clone 630att 630 virus showed some low level clinical signs when injected into dogs.

Figure 6:
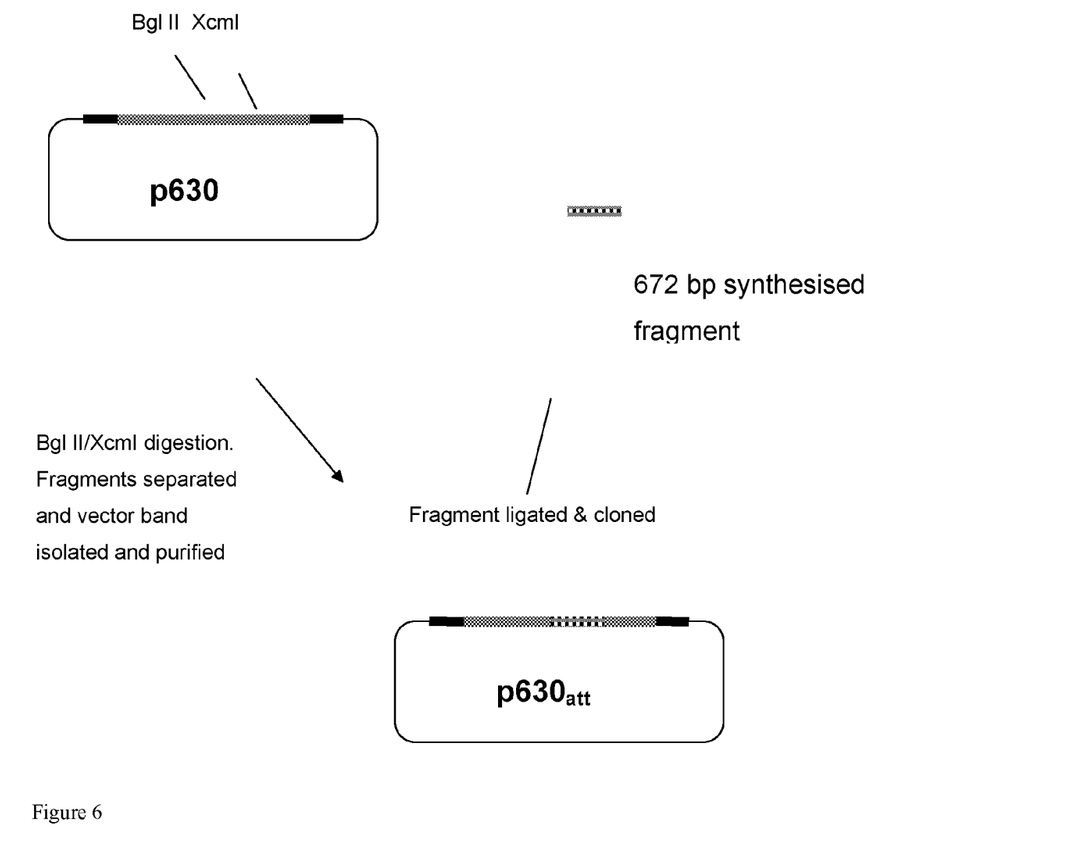
FIG. 6: Construction of p630$_{att}$

A portion of the capsid gene was chemically synthesised incorporating amino acid changes observed in Nobivac parvo C but not found to occur in field strains. This fragment was then substituted for the same region in plasmid p630 to create plasmid p630att; this is illustrated in FIG. 6.

The DNA sequence corresponding to that between positions 3356 and 4029 on the CPV genome was synthesised. The exact DNA sequence, provided here as SEQ ID NO: 2, is shown below

```
  1 agatctgaga cattgggttt ttatccatgg aaaccaacca
    taccaactcc atggagatat tattttcaat gggatagaac
    attagtacca tctcatactg 101 gaactagtgg cacaccaaca aatatatacc atggtacaga
    tccagatgat gttcaatttt atactattga aaattctgtg
    ccagtacact tactaagaac 201 aggtgatgaa tttgctacag gaacattttt ttttgattgt
    aaaccatgta gactaacaca tacatggcaa acaaatagag
    cattgggctt accaccattt 301 ctaaattctt tgcctcaagc tgaaggaggt actaactttg
    gttatatagg agttcaacaa gataaaagac gtggtgtaac
    tcaaatggga aatacaaact 401 atattactga agctactatt atgagaccag ctgaggttgg
    ttatagtgca ccatattatt cttttgaggc gtctacacaa
    gggccattta aaacacctat 501 tgcagcagga cgggggggag cgcaaacaga tgaaaatcaa
    gcagcagatg gtgatccaag atatgcattt ggtagacaac
    atggtaaaaa aactaccaca 601 acaggagaaa cacctgagag atttacatat atagcacatc
    aagatacagg aagatatcca gaaggagatt gg
```

The restriction enzyme sites Bgl II and XcmI are shown in bold and underlined.

The sequence was liberated from the plasmid in which it was provided by digestion with Bgl II and XcmI. The DNA fragments were separated by agarose gel electrophoresis and the 672 by fragment was isolated and purified.

Transfection of A72 or CrFK cells with p630att resulted in the generation of infectious virus (630att) which when administered to pups gave no clinical signs.

In a comparative study, a vaccine comprising clone 630 and a vaccine comprising clone 630att were compared.

Five MDA negative dogs were vaccinated subcutaneous $10^{8.0}$-$10^{8.3}$ TCID$_{50}$ of Clone 630 in 1 ml. This led to mild to moderate signs in all dogs. Weight change over 5 day period was −6% on average in 5 dogs, as follows from the table below.

|  |  | day −1 | day +3 | day +4 | day +5 | Change |
|---|---|---|---|---|---|---|
| Clone 630 | 964 | 7145 | 6740 | 6440 | 6650 | −7 |
|  | 320 | 7840 | 7625 | 7270 | 7060 | −10 |
|  | 148 | 6115 | 5915 | 5665 | 5740 | −6 |
|  | 761 | 5740 | 5525 | 5595 | 5530 | −4 |
|  | 959 | 5040 | 4890 | 5030 | 4910 | −3 |
|  | Mean | 6376 | 6139 | 6000 | 5978 | −6 |

Five MDA negative dogs were vaccinated subcutaneous $10^{8.0}$-$10^{8.3}$ TCID$_{50}$ of Clone 630att in 1 ml.

In this group, no clinical symptoms, no temperature rises, no leukopaenia, no diarrhoea or vomiting was seen. Moreover, there was a substantial weight gain in this group, as follows from the table below.

| | % Weight Gain | | |
|---|---|---|---|
| | Days −4 to 0 | Days 0 to +7 | Days +7 to +14 |
| Group 1 | 7 | 13 | 11 |
| 630att | | | 15 |

It was therefore concluded that vaccines on the basis of clone 630att indeed behave attenuated when compared to clone 630, and have an excellent safety profile.

Example 2

Generation of a Recombinant Virus Having an Attenuating Mutation Outside the Capsid Gene Strain 154 att was obtained from a commercially available Nobivac Parvo C (Intervet Schering-Plough Animal Health) and strain Jess was a field isolate of a type 2c virus.

Viruses were grown on adherent canine or feline kidney cells (e.g. A72 & CrFK) using M6B8 medium containing 5% fetal calf serum. Replicative form (RF) DNA was prepared from infected cell cultures using a modification of the standard "Hirt" method (McMaster et al 1981).

RF DNA prepared from the 154 att strain was digested with the restriction enzyme PstI and the fragments separated by agarose gel electrophoresis. The 3055 base pair (bp) band (corresponding to the left hand end of CPV) was excised from the gel and purified using Qiagen Qiaquick gel extraction columns. RF DNA isolated from CPV Jess infected cells was digested with the restriction enzyme XmnI. Again the DNA fragments were separated by agarose gel electrophoresis followed by purification of an approximately 2750 by band (corresponding to the right hand end of CPV including the capsid sequence) using Qiagen Qiaquick gel extraction columns.

The purified 3055 by and 2750bp fragments from 154att and Jess were combined and transfected into A72 or CrFK cells in culture. Transfections were performed using Lipofectamine 2000 (Invitrogen) with approximately 3 μg of each fragment, following the manufactures instructions.

Following transfection, cells were passaged and monitored by haemagglutination (HA) assay. Virus was detected by HA at pass 4. DNA sequence determination of hybrid viruses was performed using standard DNA sequencing protocols using either RF DNA or PCR fragment templates. Virus was purified by limiting dilution on adherent susceptible canine or feline cells.

Example 3

Recombinant Virus Constructed from Cloned Viral DNA

Recombinant virus was generated from cloned fragments. The genome of virus strain 154att was cloned into the standard cloning vector pBluescript (Stratagene inc.). In order to maintain the palindromic terminal sequences intact the plasmid was propagated in the bacterial host DL795 which is defective in a number of recombination systems. Cloning of parvovirus genomes has been described in the literature and the techniques required are known to someone skilled in the art. The obtained clone of 154att (p 154att) was digested with the restriction enzyme Pac I such that the digestion was not allowed to go to completion, i.e. the restriction enzyme digest was only partial. The digested fragments were then subjected to digestion with the restriction enzyme Xmn I. The digested DNA fragments were then separated by agarose gel electrophoresis and the fragment indicated in the diagram below was excised from the gel and purified using Qiagen Qiaquick gel extraction columns. The Xmn I and right hand Pac sites flank the capsid region in the parvovirus genome.

Figure 8:
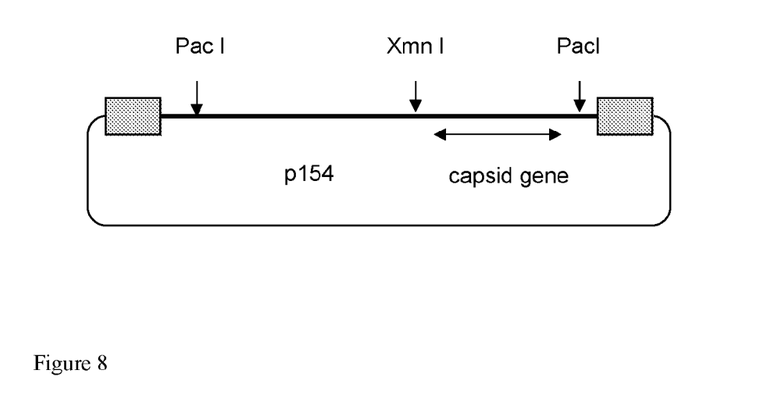
FIG. 8: schematic representation of the infectious plasmid clone of CPV strain 154att showing the restriction enzyme sites Pac I and Xmn I. The shaded boxes illustrate the terminal palindrome sequences

The capsid gene of 154 att was replaced by the capsid gene of a virulent strain of CPV as follows. The Xmn I site and the right hand Pac I indicated in FIG. 8 lie outside the boundaries of the capsid gene. The approximately 110bp sequence between the Pac I site and the end of the capsid gene differs significantly between the 154att strain and virulent isolates. There are as yet no recorded sequence changes in the short sequence (~55 bp) between the Xmn I site and the start of the capsid gene. Therefore in order to limit the exchange of material just to the capsid sequence; the virulent CPV capsid sequence was chemically synthesized and vaccine specific sequence between the PacI site and the capsid stop signal was retained.

Below, the chemically synthesized sequence is shown containing the CPV capsid gene. The sequence as shown below is provided herein as SEQ ID NO: 3.

```
AGAGGCAGACCTGAGAGCCATCTTTACTTCTGAACAATTGGAAGAAGATTTTCGAGA
                                             Xmn I

CGACTTGGATTAAGGTACGATGGCACCTCCGGCAAAGAGAGCCAGGAGAGGTAAGGGTGT

GTTAGTAAAGTGGGGGAGAGGAAAGATTTAATAACTTAACTAAGTATGTGTTTTTTTAT

AGGACTTGTGCCTCCAGGTTATAAATATCTTGGGCCTGGGAACAGTCTTGACCAAGGAGA

ACCAACTAACCCTTCTGACGCCGCTGCAAAAGAACACGACGAAGCTTACGCTGCTTATCT

TCGCTCTGGTAAAAACCCATACTTATATTTCTCGCCAGCAGATCAACGCTTTATAGATCA

AACTAAGGACGCTAAAGATTGGGGGGGGAAAATAGGACATTATTTTTTTAGAGCTAAAAA

GGCAATTGCTCCAGTATTAACTGATACACCAGATCATCCATCAACATCAAGACCAACAAA
```

-continued

```
ACCAACTAAAAGAAGTAAACCACCACCTCATATTTTCATTAATCTTGCAAAAAAAAAAA

AGCCGGTGCAGGACAAGTAAAAAGAGACAATCTTGCACCAATGAGTGATGGAGCAGTTCA

ACCAGACGGTGGTCAACCTGCTGTCAGAAATGAAAGAGCAACAGGATCTGGGAACGGGTC

TGGAGGCGGGGGTGGTGGTGGTTCTGGGGGTGTGGGGATTTCTACGGGTACTTTCAATAA

TCAGACGGAATTTAAATTTTTGGAAAACGGATGGGTGGAAATCACAGCAAACTCAAGCAG

ACTTGTACATTTAAATATGCCAGAAAGTGAAAATTATAGAAGAGTGGTTGTAAATAATTT

GGATAAAACTGCAGTTAACGGAAACATGGCTTTAGATGATACTCATGCACAAATTGTAAC

ACCTTGGTCATTGGTTGATGCAAATGCTTGGGGAGTTTGGTTTAATCCAGGAGATTGGCA

ACTAATTGTTAATACTATGAGTGAGTTGCATTTAGTTAGTTTTGAACAAGAAATTTTTAA

TGTTGTTTTAAAGACTGTTTCAGAATCTGCTACTCAGCCACCAACTAAAGTTTATAATAA

TGATTTAACTGCATCATTGATGGTTGCATTAGATAGTAATAATACTATGCCATTTACTCC

AGCAGCTATGAGATCTGAGACATTGGGTTTTTATCCATGGAAACCAACCATACCAACTCC

ATGGAGATATTATTTTCAATGGGATAGAACATTAATACCATCTCATACTGGAACTAGTGG

CACACCAACAAATATATACCATGGTACAGATCCAGATGATGTTCAATTTTATACTATTGA

AAATTCTGTGCCAGTACACTTACTAAGAACAGGTGATGAATTTGCTACAGGAACATTTTT

TTTTGATTGTAAACCATGTAGACTAACACATACATGGCAAACAAATAGAGCATTGGGCTT

ACCACCATTTCTAAATTCTTTGCCTCAAGCTGAAGGAGGTACTAACTTTGGTTATATAGG

AGTTCAACAAGATAAAAGACGTGGTGTAACTCAAATGGGAAATACAAACTATATTACTGA

AGCTACTATTATGAGACCAGCTGAGGTTGGTTATAGTGCACCATATTATTCTTTTGAGGC

GTCTACACAAGGGCCATTTAAAACACCTATTGCAGCAGGACGGGGGGGAGCGCAAACAGA

TGAAAATCAAGCAGCAGATGGTGATCCAAGATATGCATTTGGTAGACAACATGGTCAAAA

AACTACCACAACAGGAGAAACACCTGAGAGATTTACATATATAGCACATCAAGATACAGG

AAGATATCCAGAAGGAGATTGGATTCAAAATATTAACTTTAACCTTCCTGTAACAGAAGA

TAATGTATTGCTACCAACAGATCCAATTGGAGGTAAAACAGGAATTAACTATACTAATAT

ATTTAATACTTATGGTCCTTTAACTGCATTAAATAATGTACCACCAGTTTATCCAAATGG

TCAAATTTGGGATAAAGAATTTGATACTGACTTAAAACCAAGACTTCATGTAAATGCACC

ATTTGTTTGTCAAAATAATTGTCCTGGTCAATTATTTGTAAAAGTTGCGCCTAATTTAAC

AAATGAATATGATCCTGATGCATCTGCTAATATGTCAAGAATTGTAACTTACTCAGATTT

TTGGTGGAAAGGTAAATTAGTATTTAAAGCTAAACTAAGAGCCTCTCATACTTGGAATCC

AATTCAACAAATGAGTATTAATGTAGATAACCAATTTAACTATGTACCAAGTAATATTGG

AGGTATGAAAATTGTATATGAAAAATCTCAGCTAGCACCTAGAAAATTATAT<u>TAA</u>CATAC

TTACTATGTTTTTATGTTTATTACATATCAACTAACACCTAGAAAATTATATTAATATAC

TTACTATGTTTTTATGTTTATTACATATTATTTTAAGATTAATTAAGGCGCGCC
                                     Pac I
```

The Xmn I & Pac I sites are indicated and underlined. The stop codon (TAA) of the capsid coding region The capsid (Vp1/Vp2) coding sequence is in bold.

Figure 9:
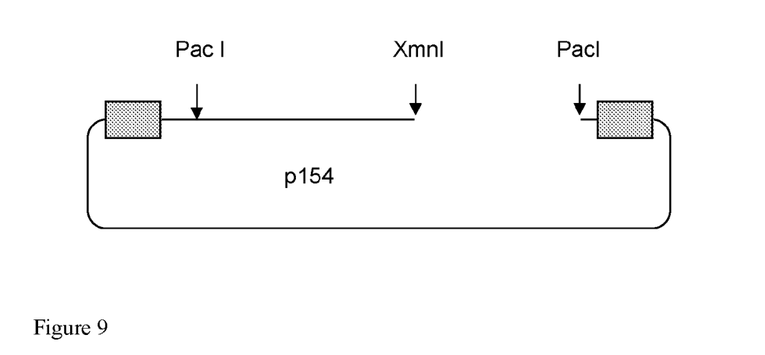
FIG. 9: schematic showing the selected product of the partial Pac I/Xmn I digest that was selected for further manipulation
Figure 10:
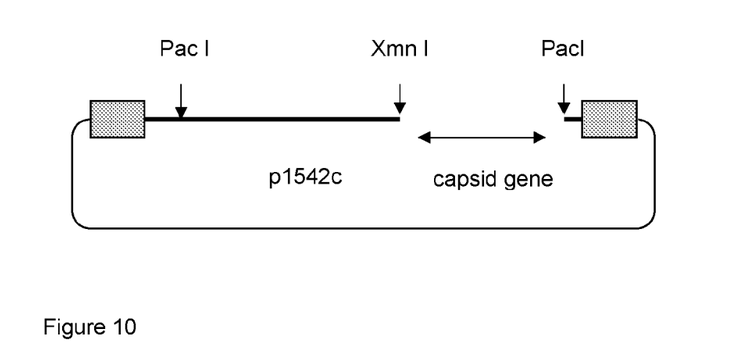
FIG. 10: plasmid containing the 154att vaccine virus DNA in which the capsid gene is substituted by a virulent CPV2c capsid sequence.

The synthesized fragment was liberated from the plasmid in which it was provided using the enzymes Xmn I and Pac I, it was then ligated to the fragment shown in FIG. 9. Competent E. coli (strain DL795) was transformed with the ligation mix using standard protocols and bacteria harboring the recombinant plasmids isolated and identified. The resultant plasmid p1542c illustrated below (FIG. 10) was then prepared from the cloned E. coli.

Hybrid virus was prepared as follows. Plasmid p1542c DNA was transfected into A72 or CrFK cells in culture. Transfections were performed using Lipofectamine 2000 (Invitrogen) with approximately 3 microgram of DNA, following the manufacturer's instructions. Following transfection, cells were passaged and monitored by haemagglutination (HA) assay. Virus was detected by HA at pass 4. DNA sequence determination of hybrid viruses was performed using standard DNA sequencing protocols using either RF DNA or PCR fragment templates. Virus was purified by limiting dilution on adherent susceptible canine or feline cells.

The invention claimed is:

1. A live attenuated canine parvovirus type 2 (CPV2), wherein said CPV2 comprises a capsid gene coding for both an amino acid other than isoleucine at amino acid position 219 of the capsid protein and an amino acid other than glutamine at amino acid position 386 of the capsid protein; wherein a DNA fragment of a part of the non-capsid region of said CPV2 is replaced by a homologous DNA fragment of a part of the non-capsid region derived from a second parvovirus, wherein said second parvovirus is a canine parvovirus 2, and wherein said homologous DNA fragment of said second parvovirus carries an attenuating mutation in the nonstructural region in the region from position 2061 to 2072, due to the replacement of the DNA sequence of wild-type CPV2 in the region from position 2061 to 2072 encoding the amino acid sequence LTPL (SEQ ID NO: 6) with a DNA sequence encoding the amino acid sequence HVRM (SEQ ID NO: 7).

2. A vaccine for protecting an animal against parvovirus, comprising the live attenuated CPV2 of claim 1 and a pharmaceutically acceptable carrier.

3. A method for treating an animal comprising administering to said animal the live attenuated CPV2 of claim 1.

4. The live attenuated CPV2 according to claim 1 that encodes a capsid protein of CPV2 serotype 2a, 2b, or 2c, or a capsid protein from feline parvovirus.

5. A vaccine for protecting an animal against parvovirus, comprising the live attenuated CPV2 of claim 4 and a pharmaceutically acceptable carrier.

6. A combination vaccine for the protection of animals against pathogens, characterized in that said combination vaccine comprises a vaccine according to claim 5 and an additional antigen of a virus or micro-organism pathogenic to animals or genetic information encoding an immunogenic protein of said virus or micro-organism.

7. A combination vaccine according to claim 6, characterized in that said virus or micro-organism pathogenic to animals is selected from the group consisting of *Ehrlichia canis, Babesia gibsoni, vogeli, rossi, Leishmania donovani*-complex, Canine adenovirus, Canine coronavirus, Canine distempervirus, *Leptospira interrogans serovar canicola, icterohaemorrhagiae, pomona, grippotyphosa, Bratislava,* Canine hepatitisvirus, Canine parainfluenzavirus, rabies virus, *Hepatozoon canis, Borrelia burgdorferi, Bordetella bronchiseptica,* feline Herpesvirus, feline calicivirus, feline panleucopenia and *Chlamydophila felis.*

8. A method for making the vaccine of claim 5, comprising mixing the live attenuated CPV2 with a pharmaceutically acceptable carrier.

9. A method of protecting an animal against parvovirus infection comprising administering to the animal the vaccine of claim 5.

10. The live attenuated CPV2 according to claim 1, wherein said CPV2 comprises a capsid gene coding for a valine at amino acid position 219 of the capsid protein, a lysine at amino acid position 386 of the capsid protein, or both a valine at amino acid position 219 of the capsid protein and a lysine at amino acid position 386 of the capsid protein.

11. A vaccine for protecting an animal against parvovirus, comprising the live attenuated CPV2 of claim 10 and a pharmaceutically acceptable carrier.

12. The live attenuated CPV2 according to claim 10, wherein said CPV2 comprises a capsid gene coding for a valine at amino acid position 219 of the capsid protein and a lysine at amino acid position 386 of the capsid protein.

13. A vaccine for protecting an animal against parvovirus, comprising the live attenuated CPV2 of claim 12 and a pharmaceutically acceptable carrier.

14. A method of using recombinant DNA techniques to make the live attenuated CPV2 of claim 12 comprising altering both a codon of the capsid gene that encodes the isoleucine at amino acid position 219 to encode an amino acid other than isoleucine and a codon of the capsid gene that encodes the glutamine at amino acid position 386 to encode an amino acid other than glutamine.

15. A method for preparing the live attenuated CPV2 of claim 12 comprising both exchanging a DNA fragment encoding at least part of the CPV2 capsid protein comprising a codon encoding isoleucine at amino acid position 219 with a DNA fragment encoding the same part of the capsid protein comprising a codon encoding an amino acid other than isoleucine at amino acid position 219, and exchanging a DNA fragment encoding at least part of the CPV2 capsid protein comprising a codon encoding glutamine at amino acid position 386 with a DNA fragment encoding the same part of the capsid protein comprising a codon encoding an amino acid other than glutamine at amino acid position 386.

16. The live attenuated CPV2 according to claim 12 that encodes a capsid protein of CPV2 serotype 2a, 2b, or 2c, or a capsid protein from feline parvovirus.

17. A vaccine for protecting an animal against parvovirus, comprising the live attenuated CPV2 of claim 16 and a pharmaceutically acceptable carrier.

* * * * *

SEQUENCE LISTING

```
<160> NUMBER OF SEQ ID NOS: 7

<210> SEQ ID NO 1
<211> LENGTH: 5003
<212> TYPE: DNA
<213> ORGANISM: canine parvovirus

<400> SEQUENCE: 1
atcaatgttt agaaccaact gaccaagttc acgtacgtat gacgtgatga cgcgcgctgc      60
gcgcgctgcc tacggcagtc acacgtcata cgtacgctcc ttggtcagtt ggttctaaag     120
aatgataggc ggtttgtgtg tttaaacttg ggcgggaaaa ggtggcgggc taattgtggg     180
cgtggttaaa ggtataaaag acaaaccata gaccgttact gacattcgct tcttgtcttt     240
gacagagtga acctctctta ctttgactaa ccatgtctgg caaccagtat actgaggaag     300
ttatggaggg agtaaattgg ttaaagaaac atgcagaaaa tgaagcattt tcgtttgttt     360
ttaaatgtga caacgtccaa ctaaatggaa aggatgttcg ctggaacaac tataccaaac     420
caattcaaaa tgaagagcta acatctttaa ttagaggagc acaaacagca atggatcaaa     480
ccgaagaaga agaaatggac tgggaatcgg aagttgatag tctcgccaaa aagcaagtac     540
aaacttttga tgcattaatt aaaaaatgtc tttttgaagt ctttgtttct aaaaatatag     600
aaccaaatga atgtgtttgg tttattcaac atgaatgggg aaaagatcaa ggctggcatt     660
gtcatgtttt acttcatagt aagaacttac aacaagcaac tggtaaatgg ctacgcagac     720
aaatgaatat gtattggagt agatggttgg tgactctttg ttcggtaaac ttaacaccaa     780
ctgaaaagat taagctcaga gaattgcag aagatagtga atgggtgact atattaacat     840
acagacataa gcaaacaaaa aaagactatg ttaaaatggt tcattttgga aatatgatag     900
catattactt tttaacaaag aaaaaaattg tccacatgac aaaagaaagt ggctattttt     960
taagtactga ttctggttgg aaatttaact ttatgaagta tcaagacaga caaattgtca    1020
gcacacttta cactgaacaa atgaaaccag aaaccgttga accacagtg acgacagcac    1080 aggaaacaaa gcgcgggaga attcaaacta aaaaggaagt gtcaatcaaa tgtacttgc     1140 gggacttggt tagtaaagga gtaacatcac ctgaagactg atgatgtta caaccagata    1200
```

-continued

```
gttatattga aatgatggca caaccaggag gtgaaaatct tttaaaaaat acacttgaaa    1260
tttgtacttt gactttagca agaacaaaaa cagcatttga attaatactt gaaaaagcag    1320
ataatactaa actaactaac tttgatcttg caaattctag aacatgtcaa attttagaa     1380
tgcacggatg gaattggatt aaagtttgtc acgctatagc atgtgtttta aatagacaag    1440
gtggtaaaag aaatacagtt cttttcatg gaccagcaag tacaggaaaa tctatcattg     1500
ctcaagccat agcacaagct gtgggtaatg ttggttgtta taatgcagca aatgtaaatt    1560
ttccatttaa tgactgtacc aataaaaatt taatttggat tgaagaagct ggtaactttg    1620
gtcaacaagt taatcaattt aaagcaattt gttctggaca aacaattaga attgatcaaa    1680
aaggtaaagg aagtaagcaa attgaaccaa ctccagtaat tatgacaact aatgaaaata    1740
taacaattgt gaggattgga tgtgaagaaa gacctgaaca tacacaacca ataagagaca    1800
gaatgttgaa cattaagtta gtatgtaagc ttccaggaga ctttggtttg gttgataaag    1860
aagaatggcc tttaatatgt gcatggttag ttaaacatgg ttatgaatca accatggcta    1920
actatacaca tcattgggga aaagtaccag aatgggatga aaactgggcg gagcctaaaa    1980
tacaagaagg tataaattca ccaggttgca aagacttaga gacacaagcg gcaagcaatc    2040
ctcagagtca agaccaagtt cacgtacgta tgactccgga cgtagtggac cttgcactgg    2100
aaccgtggag tactccagat acgcctattg cagaaactgc aaatcaacaa tcaaaccaac    2160
ttggcgttac tcacaaagac gtgcaagcga gtccgacgtg gtccgaaata gaggcagacc    2220
tgagagccat ctttacttct gaacaattgg aagaagattt tcgagacgac ttggattaag    2280
gtacgatggc acctccggca aagagagcca ggagaggtaa gggtgtgtta gtaaagtggg    2340
gggagaggaa agatttaata acttaactaa gtatgtgttt ttttatagga cttgtgcctc    2400
caggttataa atatcttggg cctgggaaca gtcttgacca aggagaacca actaacccctt   2460
ctgacgccgc tgcaaaagaa cacgacgaag cttacgctgc ttatcttcgc tctggtaaaa    2520
acccatactt atattttcg ccagcagatc aacgctttat agatcaaact aaggacgcta     2580
aagattgggg ggggaaaata ggacattatt tttagagc taaaaggca attgctccag        2640
tattaactga tacaccagat catccatcaa catcaagacc aacaaaacca actaaaagaa    2700
gtaaaccacc acctcatatt ttcatcaatc ttgcaaaaaa aaaaaaagcc ggtgcaggac    2760
aagtaaaaag agacaatctt gcaccaatga gtgatggagc agttcaacca gacggtggtc    2820
aacctgctgt cagaaatgaa agagctacag gatctgggaa cgggtctgga ggcggggtg    2880
gtggtggttc tggggtgtg gggatttcta cgggtacttt caataatcag acggaattta     2940
aatttttgga aaacggatgg gtggaaatca cagcaaactc aagcagactt gtacatttaa    3000
atatgccaga aagtgaaaat tatagaagag tggttgtgaa taatatggat aaaactgcag    3060
ttaacggaaa catggcttta gatgatattc atgcacaaat tgtaacacct tggtcattgg    3120
ttgatgcaaa tgcttgggga gtttggttta atccaggaga ttggcaacta attgttaata    3180
ctatgagtga gttgcattta gttagttttg aacaagaaat ttttaatgtt gttttaaaga    3240
ctgtttcaga atctgctact cagccaccaa ctaaagttta taataatgat ttaactgcat    3300
cattgatggt tgcattagat agtaataata ctatgccatt tactccagca gctatgagat    3360
ctgagacatt gggttttat ccatggaaac caaccatacc aactccatgg agatattatt     3420
ttcaatggga tagaacatta gtaccatctc atactggaac tagtggcaca ccaacaaata    3480
tataccatgg tacagatcca gatgatgttc aattttatac tattgaaaat tctgtgccag    3540
tacacttact aagaacaggt gatgaatttg ctacaggaac atttttttt gattgtaaac     3600
```

```
catgtagact aacacataca tggcaaacaa atagagcatt gggcttacca ccatttctaa    3660
attctttgcc tcaatctgaa ggagctacta actttggtga tataggagtt caacaagata    3720
aaagacgtgg tgtaactcaa atgggaaata caaactatat tactgaagct actattatga    3780
gaccagctga ggttggttat agtgcaccat attattcttt tgagacgtct acacaagggc    3840
catttaaaac acctattgca gcaggacggg ggggagcgca aacagatgaa atcaagcag     3900 cagatggtaa tccaagatat gcatttggta gacaacatgg taaaaaaact accacaacag    3960
gagaaacacc tgagagattt acatatatag cacatcaaga tacaggaaga tatccagaag    4020
gagattggat tcaaaatatt aactttaacc ttcctgtaac aaatgataat gtattgctac    4080
caacagatcc aattggaggt aaaacaggaa ttaactatac taatatattt aatacttatg    4140
gtcctttaac tgcattaaat aatgtaccac cagtttatcc aaatggtcaa atttgggata    4200
aagaatttga tactgactta aaaccaagac ttcatgtaaa tgcaccattt gtttgtcaaa    4260
ataattgtcc tggtcaatta tttgtaaaag ttgcgcctaa tttaacaaat gaatatgatc    4320
ctgatgcatc tgctaatatg tcaagaattg taacttactc agattttggt tggaaaggta    4380
aattagtatt taaagctaaa ctaagagcct ctcatacttg gaatccaatt caacaaatga    4440
gtattaatgt agataaccaa tttaactatg taccaagtaa tattggaggt atgaaaattg    4500
tatatgaaaa atctcaacta gcacctagaa aattatatta acatacttac tatgttttta    4560
tgtttattac atatcaacta acacctagaa aattatatta atatacttac tatgttttta    4620
tgtttattac atattatttt aagattaatt aaattacagc atagaaatat tgtacttgta    4680
tttgatatag gatttagaag gtttgttata tggtatacaa taactgtaag aaatagaaga    4740
acatttagat catagttagt agtttgtttt ataaaatgta ttgtaaacta ttaatgtatg    4800
ttgttatggt gtgggtggtt ggttggtttg cccttagaat atgttaagga ccaaaaaaaa    4860
tcaataaaag acatttaaaa ctaaatggcc tcgtatactg tctataaggt gaactaacct    4920
taccataagt atcaatctgt cttttagggg ggggtgggtg ggagatgcac aacatcagta    4980
gactgactgg cctggttggt tgc                                           5003

<210> SEQ ID NO 2
<211> LENGTH: 672
<212> TYPE: DNA
<213> ORGANISM: canine parvovirus

<400> SEQUENCE: 2
agatctgaga cattgggttt ttatccatgg aaaccaacca taccaactcc atggagatat     60
tattttcaat gggatagaac attagtacca tctcatactg gaactagtgg cacaccaaca    120
aatatatacc atggtacaga tccagatgat gttcaatttt atactattga aaattctgtg    180
ccagtacact tactaagaac aggtgatgaa tttgctacag gaacattttt ttttgattgt    240
aaaccatgta gactaacaca tacatggcaa acaaatagag cattgggctt accaccattt    300
ctaaattctt tgcctcaagc tgaaggaggt actaactttg ttatatagg agttcaacaa    360 gataaaagac gtggtgtaac tcaaatggga atacaaact atattactga agctactatt    420
atgagaccag ctgaggttgg ttatagtgca ccatattatt cttttgaggc gtctacacaa    480
gggccattta aaacacctat tgcagcagga cggggggag cgcaaacaga tgaaaatcaa    540
gcagcagatg gtgatccaag atatgcattt ggtagacaac atggtaaaaa aactaccaca    600
acaggagaaa cacctgagag atttacatat atagcacatc aagatacagg aagatatcca    660
```

```
gaaggagatt gg                                                         672
```

<210> SEQ ID NO 3
<211> LENGTH: 2451
<212> TYPE: DNA
<213> ORGANISM: canine parvovirus

<400> SEQUENCE: 3

```
agaggcagac ctgagagcca tctttacttc tgaacaattg gaagaagatt ttcgagacga     60
cttggattaa ggtacgatgg cacctccggc aaagagagcc aggagaggta agggtgtgtt    120
agtaaagtgg ggggagagga aagatttaat aacttaacta agtatgtgtt tttttatagg    180
acttgtgcct ccaggttata aatatcttgg gcctgggaac agtcttgacc aaggagaacc    240
aactaaccct tctgacgccg ctgcaaaaga cacgacgaa gcttacgctg cttatcttcg     300
ctctggtaaa aacccatact tatatttctc gccagcagat caacgcttta tagatcaaac    360
taaggacgct aaagattggg ggggaaaat aggacattat ttttttagag ctaaaaaggc     420
aattgctcca gtattaactg ataccaccaga tcatccatca acatcaagac caacaaaacc    480
aactaaaaga agtaaaccac cacctcatat tttcattaat cttgcaaaaa aaaaaaagc     540
cggtgcagga caagtaaaaa gagacaatct tgcaccaatg agtgatgag cagttcaacc     600
agacggtggt caacctgctg tcagaaatga aagagcaaca ggatctggga cgggtctgg    660
aggcgggggt ggtggtggtt ctgggggtgt ggggatttct acgggtactt tcaataatca    720
gacggaattt aaatttttgg aaaacggatg gtgtggaaatc acagcaaact caagcagact    780
tgtacattta aatatgccag aaagtgaaaa ttatagaaga gtggttgtaa ataatttgga    840
taaaactgca gttaacggaa acatggcttt agatgatact catgcacaaa ttgtaacacc    900
ttggtcattg gttgatgcaa atgcttgggg agtttggttt aatccaggag attggcaact    960
aattgttaat actatgagtg agttgcattt agttagtttt gaacaagaaa ttttaatgt    1020
tgttttaaag actgtttcag aatctgctac tcagccacca actaaagttt ataataatga   1080
tttaactgca tcattgatgg ttgcattaga tagtaataat actatgccat ttactccagc   1140
agctatgaga tctgagacat ggggttttta tccatggaaa ccaaccatac caactccatg   1200
gagatattat tttcaatggg atagaacatt aataccatct catactggaa ctagtggcac   1260
accaacaaat ataccatg gtacagatcc agatgatgtt caattttata ctattgaaaa    1320
ttctgtgcca gtacacttac taagaacagg tgatgaattt gctacaggaa cattttttttt   1380
tgattgtaaa ccatgtagac taacacatac atggcaaaca aatagagcat gggcttacc    1440
accattcta aattctttgc ctcaagctga aggaggtact aactttggtt atataggagt    1500
tcaacaagat aaaagacgtg gtgtaactca aatgggaaat acaaactata ttactgaagc   1560
tactattatg agaccagctg aggttggtta tagtgcacca tattattctt ttgaggcgtc   1620
tacacaaggg ccatttaaaa cacctattgc agcaggacgg gggggagcgc aaacagatga   1680
aaatcaagca gcagatggtg atccaagata tgcatttggt agacaacatg gtcaaaaaac   1740
taccacaaca ggagaaacac ctgagagatt tacatatata gcacatcaag atacaggaag   1800
atatccagaa ggagattgga ttcaaaatat taactttaac cttcctgtaa cagaagataa   1860
tgtattgcta ccaacagatc caattggagg taaaacagga attaactata ctaatatatt   1920
taatacttat ggtccttttaa ctgcattaaa taatgtacca ccagtttatc caaatggtca   1980
aatttgggat aaagaatttg atactgactt aaaaccaaga cttcatgtaa atgcaccatt   2040
tgtttgtcaa aataattgtc ctggtcaatt atttgtaaaa gttgcgccta atttaacaaa   2100
```

```
tgaatatgat cctgatgcat ctgctaatat gtcaagaatt gtaacttact cagatttttg    2160
gtggaaaggt aaattagtat ttaaagctaa actaagagcc tctcatactt ggaatccaat    2220
tcaacaaatg agtattaatg tagataacca atttaactat gtaccaagta atattggagg    2280
tatgaaaatt gtatatgaaa aatctcagct agcacctaga aaattatatt aacatactta    2340
ctatgttttt atgtttatta catatcaact aacacctaga aaattatatt aatatactta    2400
ctatgttttt atgtttatta catattattt taagattaat taaggcgcgc c            2451

<210> SEQ ID NO 4
<211> LENGTH: 16
<212> TYPE: PRT
<213> ORGANISM: canine parvovirus

<400> SEQUENCE: 4

Tyr Phe Gln Trp Asp Arg Thr Leu Val Pro Ser His Thr Gly Thr Ser
1               5                   10                  15

<210> SEQ ID NO 5
<211> LENGTH: 16
<212> TYPE: PRT
<213> ORGANISM: canine parvovirus

<400> SEQUENCE: 5

Tyr Ala Phe Gly Arg Gln His Gly Lys Lys Thr Thr Thr Thr Gly Glu
1               5                   10                  15

<210> SEQ ID NO 6
<211> LENGTH: 4
<212> TYPE: PRT
<213> ORGANISM: canine parvovirus

<400> SEQUENCE: 6

Leu Thr Pro Leu
1

<210> SEQ ID NO 7
<211> LENGTH: 4
<212> TYPE: PRT
<213> ORGANISM: canine parvovirus

<400> SEQUENCE: 7

His Val Arg Met
1
```